United States Patent [19]
Kim et al.

[11] Patent Number: 6,137,583
[45] Date of Patent: Oct. 24, 2000

[54] METHOD OF MEASURING THE DEGREE OF ALLOYING OF A GALVANIZED STEEL SHEET USING LASER BEAMS

[75] Inventors: Dal Woo Kim; Choong Soo Lim; Ki Jang Oh, all of Kyungsangbook-do, Rep. of Korea

[73] Assignee: Pohang Iron & Steel Co., Ltd., Rep. of Korea

[21] Appl. No.: 09/220,634

[22] Filed: Dec. 24, 1998

[30]     Foreign Application Priority Data

Dec. 26, 1997 [KR]   Rep. of Korea ................ 97-74220

[51] Int. Cl.$^7$ .................................................. G01N 21/55
[52] U.S. Cl. ............................................................. 356/445
[58] Field of Search .................................. 356/445, 446, 356/237.2

[56]            References Cited

FOREIGN PATENT DOCUMENTS 4-370709 of 1992  Japan .
   5-045305 of 1993  Japan .
   0044522  of 1996  Rep. of Korea .

*Primary Examiner*—Frank G. Font
*Assistant Examiner*—Zandra V. Smith

*Attorney, Agent, or Firm*—Webb Ziesenheim Logsdon Orkin & Hanson, P.C.

[57]                ABSTRACT

A method of measuring the degree of alloying of galvanized steel sheet through the use of laser beams includes the steps of directing a laser beam on a standard sample and reflecting and splitting the beam and detecting the intensity of specular reflection $I_0(\alpha)$ at an angle of reflection ($\alpha$) and the intensity of scattering $I_0(\beta)$ at an angle of reflection ($\beta$) to thus obtain the degree of alloying ($X_0$) of the standard sample by the formula:

$$X_0(\%) = k \frac{\frac{I_0(\alpha)}{I_0(\beta)}}{I_0(\alpha)}$$

The above steps are repeated to obtain values $I_1(\alpha)$ and $I_2(\beta)$ to obtain a comparative degree of alloying ($X_1$) of the standard sample using the above equation form. The arrangement of the laser, mirror and first and second beam splitters are corrected based on a comparison of the $X_0$ and $X_1$ values. The above steps are then repeated by directing the laser onto a galvanized steel sheet to obtain the degree of alloying ($X_2$) of the galvanized steel sheet.

8 Claims, 8 Drawing Sheets

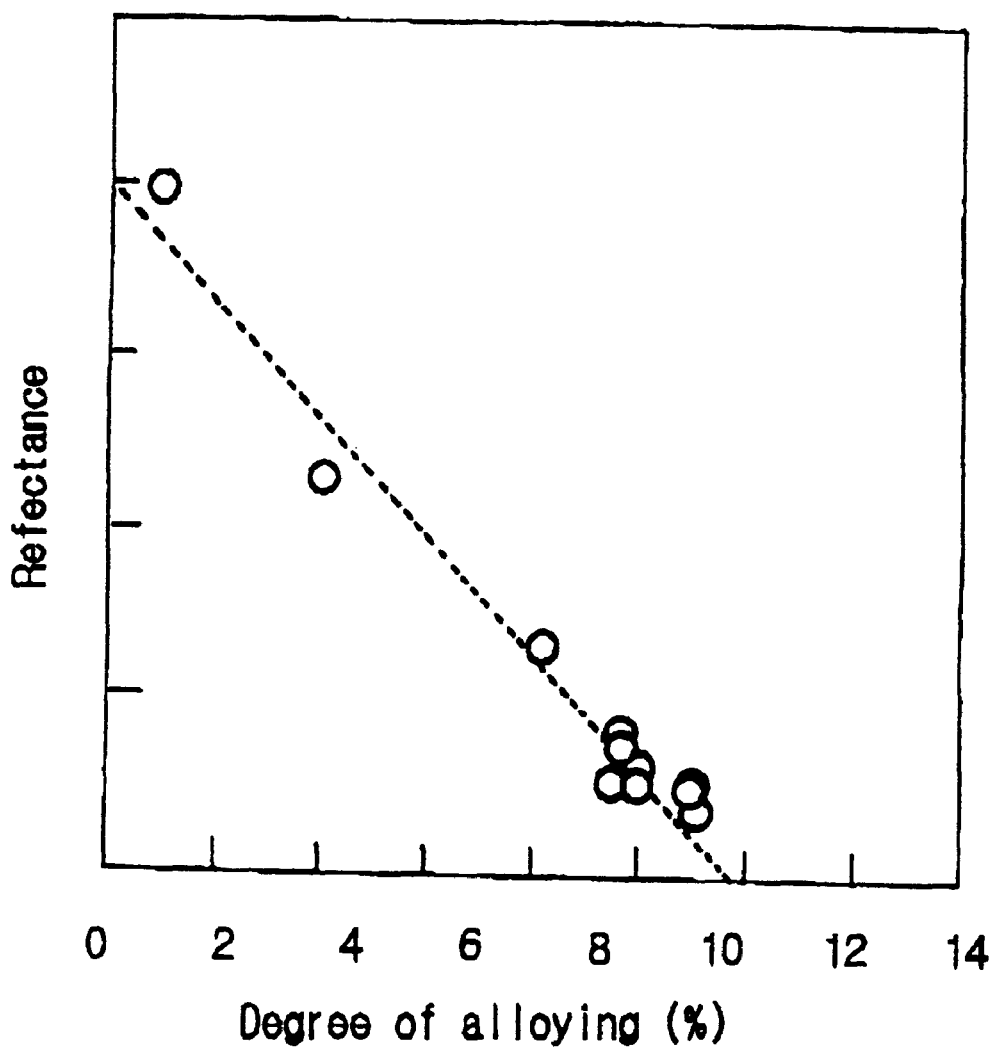

METHOD OF MEASURING THE DEGREE OF ALLOYING OF A GALVANIZED STEEL SHEET USING LASER BEAMS

BACKGROUND OF THE INVENTION

1. Field of the Invention

The present invention is related to a method of measuring the degree of alloying of a galvanized steel sheet in the non-contact type by using laser beams. In more detail, the present invention is related to a method of measuring the degree of alloying by using laser beams by which precise measurement of the degree of alloying is enabled without errors coming from surface roughness and vibration of the galvanized steel sheet by using the photodiode arrays when measuring the intensity of the laser beam reflected from the galvanized steel sheet.

2. Description of the Prior Art

Galvanized steel sheets have been widely used for constructional materials, structural articles, and other objects. Particularly, the melt zinc galvanized steel sheet which is alloyed through the heat treatment process has superior anti-corrosiveness, weldability, coating property, etc., and thus demands for its application to home appliances and industry have been increased.

However, since such superior characteristics of the alloyed melt zinc galvanized steel sheet are greatly affected by the degree of alloying of the galvanized layer, i.e., the content of Fe component in the galvanized layer, it is necessary to manage the degree of alloying consistently for securing the quality of the produced steel sheet such that a proper degree of alloying is maintained suitably for its application objects.

Particularly, in these days wherein mass-production is common, it is necessary to control the alloying process in real time so as to prevent manufacture of inferior products and ensure superior quality of them so that it is essential to carry out an on-line measurement for the degree of alloying.

As one of the methods of measuring the degree of alloying of the galvanized steel sheet, a method using x-ray diffraction has been known, and is disclosed in Japanese Patent Application Publication (No. hei 5-45305). In this method, the degree of alloying is measured by detecting the intensity of diffraction differentiated from a melt zinc galvanized steel sheet, in which differentiated diffraction has a certain angle depending on the phases of Fe and Zn which are formed as the melt zinc galvanized layer is alloyed. In this method, however, the measuring angle and position of a photodiode for detecting the intensity of diffraction affect most greatly the accuracy of the results of the measurement. Therefore, there may be a problem that even if the location of a measuring object is changed slightly, the results of the measurement differ greatly.

That is, if the above-described measurement method is supplied to actual work, it is very likely that measurement errors occur due to the vibration generated when the steel sheet is moved over roll. Moreover, since the above-described method employs x-ray, there are problems that it is difficult to apply the method to the case of working at a high temperature, and safety measures have to be considered accordingly.

Further, as another method for measuring the degree of alloying of a galvanized steel sheet, there is a method using the characteristics of the melt zinc galvanized steel sheet in that its color is changed according to the degree of alloying, which is disclosed in Japanese Patent Publication (No. hei 4-370709). The method presented in the above publication is as follows: first, photograph the enlarged picture of the surface of the steel galvanized layer,, and compare the average brightness of the enlarged picture with the degree of alloying of the galvanized layer repeatedly. And then measure the degree of alloying by preparing a comparison chart between the average brightness of the enlarged picture and the degree of alloying of the galvanized layer. That is, when measuring the degree of alloying of an unknown galvanized steel sheet in this method, the average brightness is calculated by photographing the enlarged picture of the surface of the steel sheet, and then the degree of alloying is determined by comparing the average brightness thus obtained with the value of the comparison chart which has been made previously.

This method is advantageous in that this method is less affected by the vibration compared to measuring the degree of alloying by x-ray diffraction, but still has a problem that there may occur errors in the measurement according to the surrounding illumination state and surface roughness of the galvanized layer.

Accordingly, the present inventors have conducted researches on and suggested a method of measuring the degree of alloying by using laser beams which are applicable properly to the case of working at a high temperature, enable safer measurement of the degree of alloying, and is less affected by the surrounding illumination state and the change in the surface roughness of the galvanized layer. The results of their study are summarized in Korean Patent Application No. 96-44522, which is illustrated below with reference to FIG. 1.

In this method, firstly, a standard sample is installed inside of a measuring instrument (100), and the intensity of specular reflection $I_0(\alpha)$ and that of scattering $I_0(\beta)$ are detected. The basic degree of alloying ($X_0$) of the standard sample is obtained by substituting the intensity of specular reflection $I_0(\alpha)$ and that of scattering $I_0(\beta)$ into Equation (1):

$$X_0(\%) = k \ln \frac{\frac{I_0(\alpha)}{I_0(\beta)}}{I_0(\alpha)} \qquad (1)$$

The intensity of specular reflection $I_1(\alpha)$ and that of scattering $I_1(\beta)$ of the standard sample (113) are detected, and the comparative degree of alloying ($X_1$) of the standard sample is obtained by substituting the intensity of specular reflection $I_1(\alpha)$ and that of scattering $I_1(\beta)$ thus detected into Equation (1).

The arrangement of a laser generator (101), a first beam splitter (102), and a mirror (104) is corrected by comparing the basic degree of alloying ($X_0$) and the comparative degree of alloying ($X_1$) of the standard sample thus obtained. Then the degree of alloying ($X_2$) of the galvanized steel sheet (109) is obtained by detecting the intensity of specular reflection $I_2(\alpha)$ and that of scattering $I_2(\beta)$ of the galvanized steel sheet (109) and substituting $I_2(\alpha)$ and $I_2(\beta)$ thus detected into Equation (1). In the meantime, reference numerals 103, 105, 106, 112, and 113 in FIG. 1 not illustrated here show photodetectors.

However, the above-described method of measuring the degree of alloying by using laser beams is problematic in that it is difficult to measure the degree of alloying precisely if the galvanized steel sheet, which is an object of measurement, is inclined by external vibration.

Also, during the on-line measurement of the degree of alloying of a galvanized steel sheet by using laser beams in the production line, the measurement is made while moving the measuring instrument in the widthwise direction of the galvanized steel sheet in order to obtain information on the degree of alloying as much as possible. When desiring to obtain information on the degree of alloying in the widthwise direction of the galvanized steel sheet by moving the measuring instrument, the width of the galvanized steel sheet has to be known accurately. In the past, it was measured directly by the worker. However, this method has been problematic in that not only is it difficult to measure the width of the galvanized steel sheet during the production work, but also it is possible to have errors in measuring the widthwise degree of alloying if the width of the galvanized steel sheet is changed. Further, in this method, there are problems that if the width of the galvanized steel sheet is changed in its production line, the operation of the measuring instrument has to be stopped and re-started after inputting new information on the width of the galvanized steel sheet.

SUMMARY OF THE INVENTION

The present invention is to solve the above-described problems. It is therefore an object of the present invention to provide a method of measuring the degree of alloying using laser beams in which errors in the measurement due to external vibration of the galvanized steel sheet, of which degree of alloying is to be measured, may be eliminated.

Another object of the present invention is to provide a method of measuring the degree of alloying in which errors in the measurement by the vibration may be eliminated as well as the widthwise scanning operation of the optical instrument may be controlled automatically by finding out width of the steel sheet by detecting both ends of the galvanized steel sheet by using laser beams during the production line of the galvanized steel sheet.

The present invention to achieve one of the above-identified objects is composed of the steps of:

injecting a laser beam onto a mirror which is located at a standard position from a laser generator, dividing the laser beam reflected from the mirror into two rays at the first beam splitter which is located at the standard position, injecting one ray onto one photodiode among photodiode arrays which are formed of multiple photodiodes and arranged taking into consideration the vibration of the galvanized steel sheet, and projecting another ray through the first beam splitter and injecting onto the standard sample at an angle of incidence ($\alpha$) at the second beam splitter which is located at the standard position;

detecting the intensity of specular reflection $I_0(\alpha)$ which is reflected at an angle of reflection ($\alpha$) by the standard sample with a photodetector, and detecting the intensity of scattering $I_0(\beta)$ which is reflected at an angle of reflection ($\beta$) with another photodetector;

obtaining the basic degree of alloying ($X_0$) of the standard sample by substituting the intensity of specular reflection $I_0(\alpha)$ and the intensity of scattering $I_0(\beta)$ thus detected into Equation (2):

$$X_0(\%) = k\ln\frac{\frac{I_0(\alpha)}{I_0(\beta)}}{I_0(\alpha)} \quad (2)$$

where k is a proportional constant;

generating laser beams from the laser generator under the same conditions for those of obtaining the basic degree of alloying ($X_0$), and injecting one of beams, which are divided at the second beam splitter after passing through the mirror and the first beam splitter as described in the above, onto the standard sample at an angle of incidence ($\alpha$);

detecting the intensity of specular reflection $I_1(\alpha)$ reflected by the standard sample at an angle of reflection ($\alpha$) with a photodetector, and detecting the intensity of scattering $I_1(\beta)$ reflected at an angle of reflection ($\beta$) with another photodetector;

obtaining the comparative degree of alloying ($X_1$) of the standard sample by substituting the intensity of specular reflection $I_1(\alpha)$ and the intensity of scattering $I_1(\beta)$ thus detected into Equation (3):

$$X_1(\%) = k\ln\frac{\frac{I_1(\alpha)}{I_1(\beta)}}{I_1(\alpha)} \quad (3)$$

where k is a proportional constant;

obtaining an error between the basic degree of alloying ($X_0$) of the standard sample and the comparative degree of alloying ($X_1$) of the standard sample by comparing these two values thus obtained, and correcting the arrangement of the laser generator, mirror, first beam splitter, and second beam splitter so that this error is within a predetermined range;

generating laser beams from the laser generator under the same conditions for those of obtaining the basic degree of alloying ($X_0$), and injecting the beam, which is injected onto the second beam splitter and projected after passing through the mirror and the first beam splitter as described in the above, onto the galvanized steel sheet at an angle of incidence ($\alpha$), after correcting the arrangement of the laser generator, mirror, first beam splitter, and second beam splitter;

detecting the intensity of specular reflection $I_2(\alpha)$ reflected by the galvanized steel sheet with one photodiode among photodiode arrays which are composed of multiple photodiodes and are arranged taking into consideration of the vibration the galvanized steel sheet, and detecting the intensity of scattering $I_2(\beta)$ reflected with another photodiode among the photodiode arrays which are apart at a predetermined distance n from the photodiode by which the specular reflection is detected; and obtaining the degree of alloying ($X_2$) of the galvanized steel sheet by substituting the intensity of specular reflection $I_2(\alpha)$ and the intensity of scattering $I_2(\beta)$ thus detected into Equation (4):

$$X_2(\%) = k\ln\frac{\frac{I_2(\alpha)}{I_2(\beta)}}{I_2(\alpha)} \quad (4)$$

where k is a proportional constant.

The present invention to achieve another object of the invention is composed of the steps of:

measuring the width Wo of the galvanized steel sheet by generating laser beams from a laser generator while moving one of converging lens mounted on the linear moving stage such that a distance between two converging lenses having the same focal length (f) has L<2f, injecting said beams, which is projected through the lens, mirror, first beam splitter, and second beam splitter, onto the galvanized steel sheet while running the measuring instrument left and right once, and analyzing the intensity of reflection detected by the photodiode array;

moving one lens mounted on the linear moving stage such that the distance between the two lens is L=2f, after measuring the width Wo of the galvanized steel sheet;

penetrating laser beams through the two converging lenses, which are located at the standard position from the laser generator and are apart from each other by the distance of 2f, injecting said beams onto a mirror which is located at the standard position, dividing the laser beams reflected from the mirror into two rays at the first beam splitter which is located at the standard position, one lay being detected with one photodiode among photodiode arrays which are composed of multiple photodiodes and are arranged taking into consideration the vibration of the galvanized steel sheet, while another ray penetrating through the first beam splitter and injecting said ray onto the standard sample at the second beam splitter, which is located at the standard position, at an angle of incidence ($\alpha$);

detecting the intensity of specular reflection $I_0(\alpha)$ reflected by the standard sample at an angle of reflection ($\alpha$) with a photodetector, and detecting the intensity of scattering $I_0(\beta)$ reflected at an angle of reflection ($\beta$) with another photodetector;

obtaining the basic degree of alloying ($X_0$) of the standard sample by substituting the intensity of specular reflection $I_0(\alpha)$ and the intensity of scattering $I_0(\beta)$ thus detected into Equation (5):

$$X_0(\%) = k\ln\frac{\frac{I_0(\alpha)}{I_0(\beta)}}{I_0(\alpha)} \quad (5)$$

where k is a proportional constant;

generating laser beams from the laser generator under the same conditions for those of obtaining the basic degree of alloying ($X_0$), and injecting one of beams, which are divided at the second beam splitter after passing through the mirror and the first beam splitter as described in the above, onto the standard sample at an angle of incidence ($\alpha$);

detecting the intensity of specular reflection $I_1(\alpha)$ reflected by the standard sample at an angle of reflection ($\alpha$) with the photodetector, and detecting the intensity of scattering $I_1(\beta)$ reflected at an angle of reflection ($\beta$) with the photodetector;

obtaining the comparative degree of alloying ($X_1$) of the standard sample by substituting the intensity of specular reflection $I_1(\alpha)$ and the intensity of scattering $I_1(\beta)$ thus detected into Equation (6):

$$X_1(\%) = k\ln\frac{\frac{I_1(\alpha)}{I_1(\beta)}}{I_1(\alpha)} \quad (6)$$

where k is a proportional constant;

obtaining an error between the basic degree of alloying ($X_0$) of the standard sample and the comparative degree of alloying ($X_1$) of the standard sample by comparing these two values thus obtained, and correcting the arrangement of the laser generator, mirror, first beam splitter, and second beam splitter so that this error is within a predetermined range;

generating laser beams from the laser generator under the same conditions for those of obtaining the basic degree of alloying ($X_0$), and injecting the beam, which is injected onto the second beam splitter and projected after passing through the mirror and the first beam splitter as described in the above, onto the galvanized steel sheet at an angle of incidence ($\alpha$), after correcting the arrangement of the laser generator, mirror, first beam splitter, and second beam splitter;

detecting the intensity of specular reflection $I_2(\alpha)$ reflected by the galvanized steel sheet with one photodiode among photodiode arrays which are composed of multiple photodiodes and are arranged taking into consideration the vibration of the galvanized steel sheet, and detecting the intensity of scattering $I_2(\beta)$ reflected with another photodiode among the photodiode arrays which are apart at a predetermined distance n from the photodiode by which the specular reflection is detected;

obtaining the degree of alloying ($X_2$) of the galvanized steel sheet by substituting the intensity of specular reflection $I_2(\alpha)$ and the intensity of scattering $I_2(\beta)$ thus detected into Equation (7):

$$X_2(\%) = k\ln\frac{\frac{I_2(\alpha)}{I_2(\beta)}}{I_2(\alpha)} \quad (7)$$

where k is a proportional constant; and obtaining the degree of alloying ($X_2$) of the galvanized steel sheet continuously by repeating the above-described steps while moving the measuring instrument in the widthwise direction within the width ($W_o$).

BRIEF DESCRIPTION OF THE DRAWINGS

The foregoing and other objects, aspects, and advantages will be better understood from the following detailed description of preferred embodiments of the invention with reference to the drawings, in which:

FIG. 8 is a graph showing the results of measurement of the degree of alloying according to the measurement method of the present invention.

DETAILED DESCRIPTION OF PREFERRED EMBODIMENTS OF THE INVENTION

Figure 1:
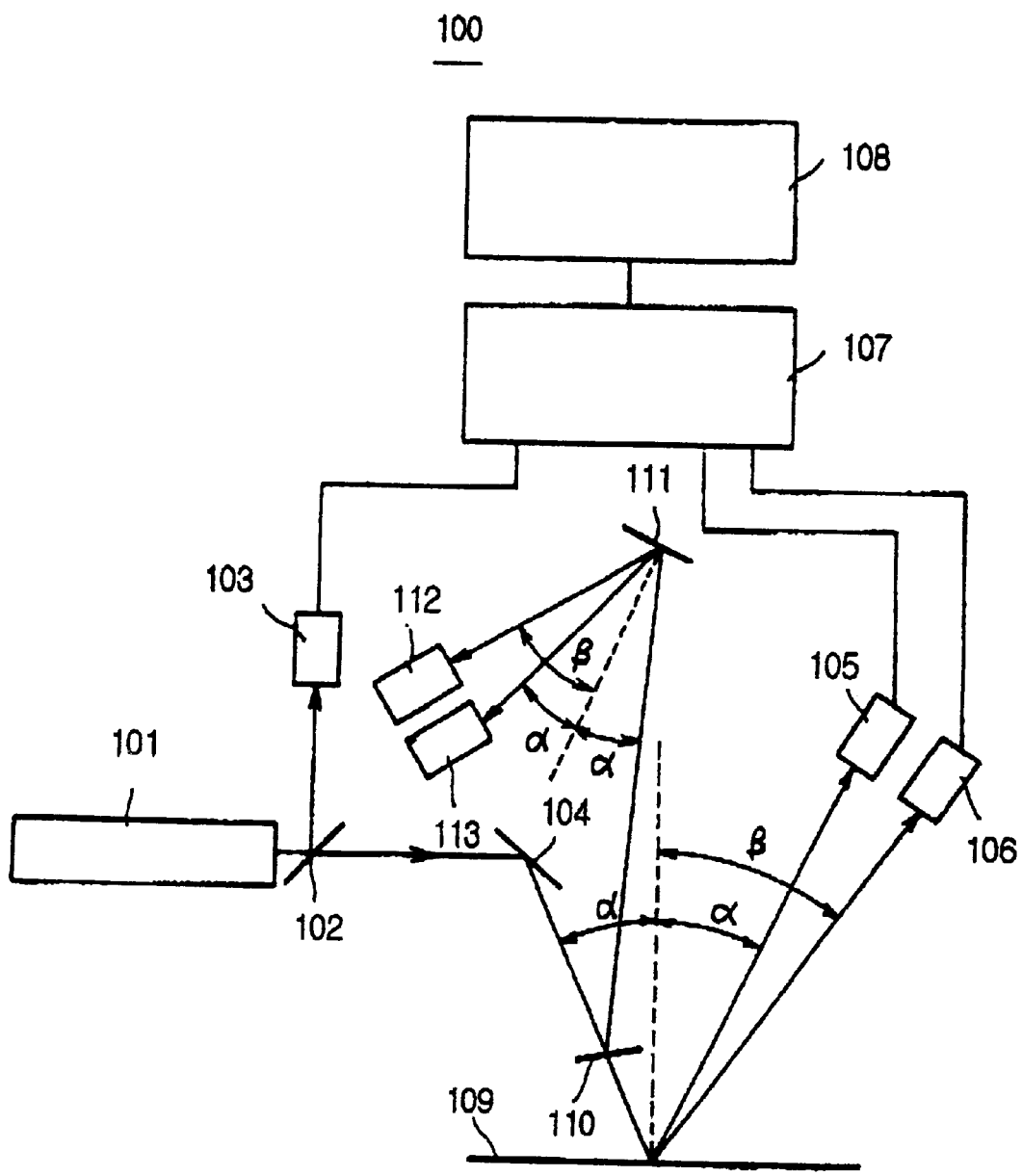
FIG. 1 is an outlined diagram of a measuring instrument for measuring the degree of alloying by using laser beams according to a prior art method.
Figure 2:
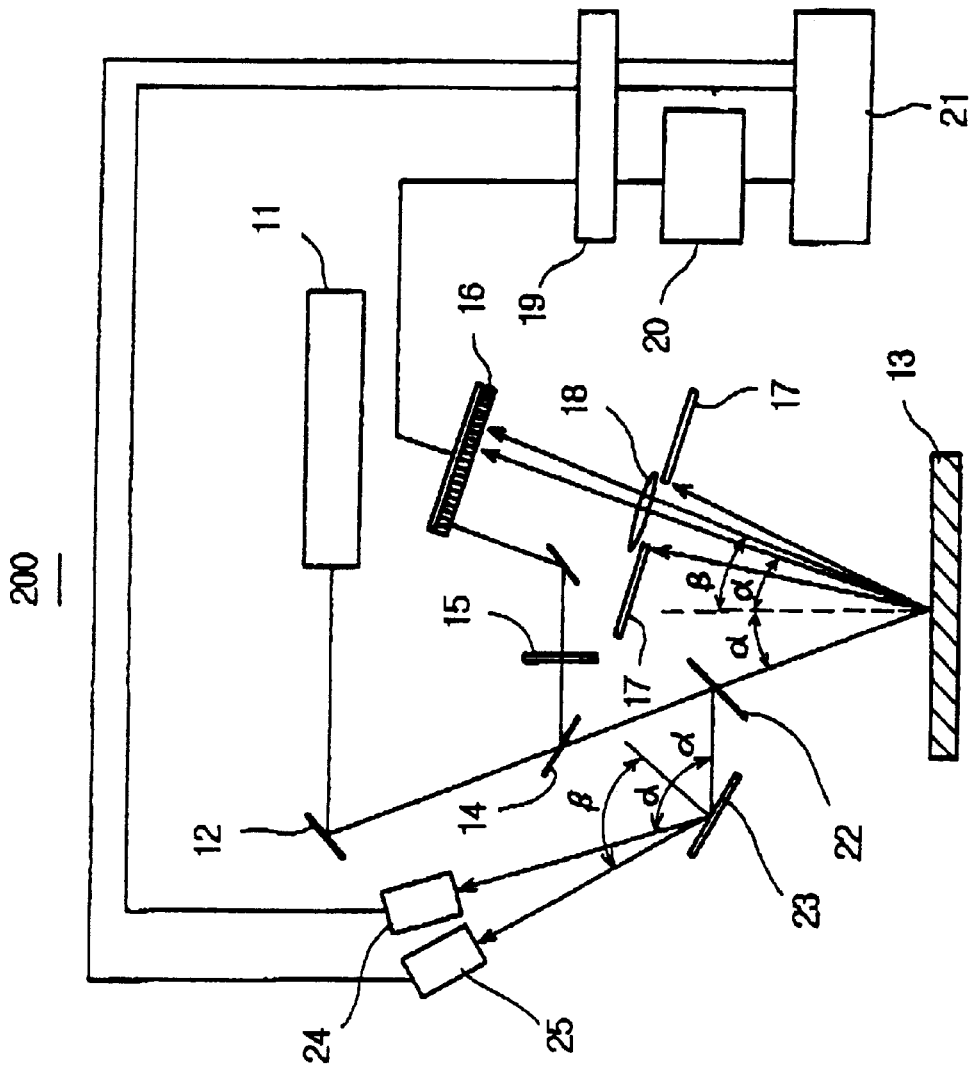
FIG. 2 is an outlined diagram of a measuring instrument for measuring the degree of alloying by using laser beams according to the present invention.

Referring now to the drawings, and more particularly to FIG. 2, there is shown a method of measuring the degree of alloying of a galvanized steel sheet using laser beams.

FIG. 2 is an outlined diagram of a measuring instrument (200) for measuring the degree of alloying by using the photodiode arrays which are formed of multiple photodiodes and arranged taking into consideration the vibration of the galvanized steel sheet in order to achieve an object of the present invention. As shown in FIG. 2, a standard sample (23) is mounted inside of the measuring instrument.

Firstly, the basic degree of alloying ($X_0$) of the standard sample is measured when the measuring instrument is regularly arranged. Then laser beams are injected onto a mirror (12) from a laser generator (11). The laser beams reflected by the mirror (12) are divided into two rays at the first beam splitter (14). One ray is reflected and detected by one photodiode among photodiode arrays (16) which are composed of multiple photodiodes and are arranged taking into consideration the vibration of the galvanized steel sheet, while another ray penetrates through the first beam splitter (14) and is injected onto the standard sample (23) at an angle of incidence ($\alpha$) at the second beam splitter (22). Here, it is desirable to have an iris (15) between the first beam splitter (14) and the photodiode array (16) in order to reduce the cross-sectional area of the incident light, and the ray detected by the photodiode array is used for correcting the change in output of the laser generator (11). The specular reflection reflected by the standard sample (23) at an angle of reflection ($\alpha$) is injected into the photodetector (24), while the scattering reflected at an angle of reflection ($\beta$) is injected into the photodetector (25). Then the basic degree of alloying ($X_0$) of the standard sample (23) is obtained by substituting the intensity of specular reflection $I_0(\alpha)$ and the intensity of scattering $I_0(\beta)$ detected by the photodetector (24) and another photodetector (25), respectively, into Equation (2). In calculating the basic degree of alloying, the intensity of rays detected by the photodetector (24) and photodetector (25) is amplified by the pre-amplifier (19), inputted to the computer (21), and calculated according to the program built in.

Next, the comparative degree of alloying ($X_1$) of the standard sample is obtained by continuously obtaining the degree of alloying of the galvanized steel sheet (13) in the same method as obtaining the basic degree of alloying ($X_0$) of the above standard sample.

In other words, laser beams of the same intensity are used, which are injected onto a mirror (12), first beam splitter (14), and second beam splitter (22). The second beam splitter (22) divides the laser beams into two rays. One ray is reflected and injected onto the standard sample (23) at an angle of incidence ($\alpha$), while another ray penetrates and is injected onto the galvanized steel sheet (13). The intensity of specular reflection $I_1(\alpha)$ reflected by the standard sample (23) at an angle of reflection ($\alpha$) is detected by the photodetector (24), while the intensity of scattering $I_1(\beta)$ reflected at an angle of reflection ($\beta$) is detected by the photodetector (25). The comparative degree of alloying ($X_1$) of the standard sample is then obtained by substituting the above values thus detected into Equation (3). The comparative degree of alloying is also calculated within the above computer (21) as in calculating the basic degree of alloying.

Then an error between the comparative degree of alloying ($X_1$) of the standard sample and the basic degree of alloying ($X_0$) of the standard sample is obtained by comparing these two values. Whether the arrangement of the laser generator (11), mirror (12), first beam splitter (14), and second beam splitter (22) is superior may be confirmed according to whether the above error is within a predetermined range.

If the arrangement is confirmed to be superior, the degree of alloying of the galvanized steel sheet (13) is obtained. On the other hand, if the arrangement is confirmed to be inferior, the arrangement of the laser generator (11), mirror (12), first beam splitter (14), and second beam splitter (22) is corrected, after which the degree of alloying of the galvanized steel sheet (13) is obtained. Such construction of the present invention can give reliability to the results of measuring the degree of alloying of the galvanized steel sheet (13).

The degree of alloying of the galvanized steel sheet (13) may be obtained simultaneously with the comparative degree of alloying ($X_1$) of the standard sample.

In obtaining the degree of alloying ($X_1$) of the standard sample, the laser beams generated from the laser generator (11) go through the mirror (12) and the first beam splitter (14), are injected onto the second beam splitter (22), are divided into two rays, and are reflected and projected. Between these, the projected ray is injected onto the galvanized steel sheet (13). The ray injected onto the galvanized steel sheet (13) at an angle of incidence ($\alpha$) is reflected by the galvanized steel sheet. The intensity of specular reflection $I_2(\alpha)$ reflected at an angle of reflection ($\alpha$) is detected by one photodiode among photodiode arrays (16) which are composed of multiple photodiodes and are arranged taking into consideration the vibration of the galvanized steel sheet, while the intensity of scattering $I_2(\beta)$ reflected at an angle of reflection ($\beta$) is detected by another photodiode among photodiode arrays (16) which are apart from the photodiode, which the specular reflection is injected into, by a predetermined distance n.

The degree of alloying ($X_2$) of the galvanized steel sheet (13) is then obtained by substituting the intensity of specular reflection $I_2(\alpha)$ and the intensity of scattering $I_2(\beta)$ which are detected by the photodiode arrays (16) into Equaiton (4). Here, since the intensity of the specular reflection $I_2(\alpha)$ is always greater than the intensity of the scattering $I_2(\beta)$, the computer (21) is able to confirm readily the photodiode by which the intensity of the specular reflection is detected, and the photodiode by which the intensity of the scattering is detected may be also determined by the predetermined distance n which is stored in the computer (21).

It is desirable to have a converging lens (18) and masks (17) at both ends of the converging lens (18) between the galvanized steel sheet (13) and photodiode arrays (16). The lens (18) converts the reflection into parallel rays, while the masks (17) pass through the specular reflection or scattering and prevent mixing of the light which is reflected by the surface of the galvanized steel sheet and the light which is reflected by the first beam splitter (14).

As described in the above, the photodiode arrays (16) are composed of arrayed multiple photodiodes. It is desirable that they are arranged in the normal direction with respect to the specular reflection which is reflected by the vibration-free galvanized steel sheet (13) at an angle of reflection ($\alpha$).

Such construction of photodiode arrays (16) is effective in eliminating errors due to vibration when measuring the degree of alloying.

The present inventors found that the degree of alloying calculated according to Equation (4) is always constant as long as the intensity of the specular reflection and that of the scattering can be measured accurately although the angles of reflection of the specular reflection and scattering are changed if the galvanized steel sheet, of which the degree of alloying is to be measured, is affected by external vibration as described below. Therefore, in providing the method of measurement of the present invention, the present inventors confirmed that the photodiode into which the scattering is injected could be determined relatively with respect to the photodiode into which the specular reflection is injected by using the photodiode arrays regardless of whether the galvanized steel sheet, of which degree of alloying is to be measured, is inclined due to the external vibration.

Figure 4A:
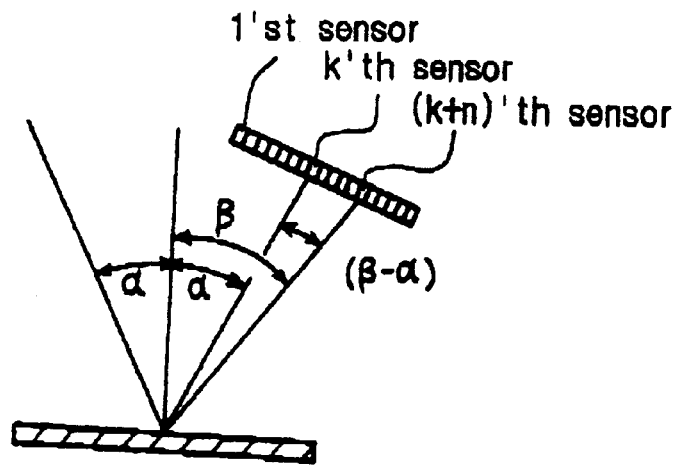
FIGS. 4(*a*), 4(*b*), and 4(*c*) show the process of eliminating an error due to vibration when measuring the degree of alloying by using the photodiode array elements according to the present invention.

In other words, as shown in FIG. 4(a), the lay (having an angle of incidence α) injected onto a galvanized steel sheet which is not affected by external vibration is reflected by the galvanized steel sheet. Among reflected rays, the most intensive specular reflection having an angle of reflection α is injected into one photodiode(k) among photodiode arrays, while the scattering reflected at an angle of reflection β is injected into another photodiode (k+n) among photodiode arrays. Here, the discrete distance between the photodiode (k) detecting the intensity of the specular reflection and the photodiode (k+n) detecting the intensity of scattering is n, which is stored in the computer (21) as a predetermined value.

Figure 4B:
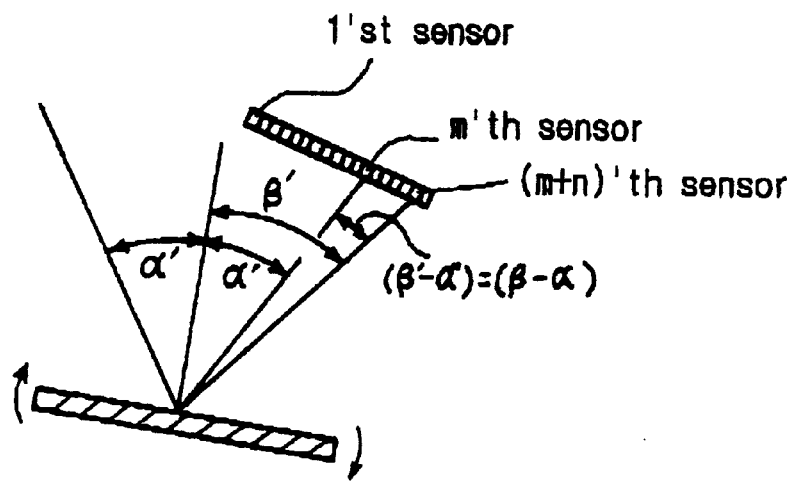
Figure 4C:
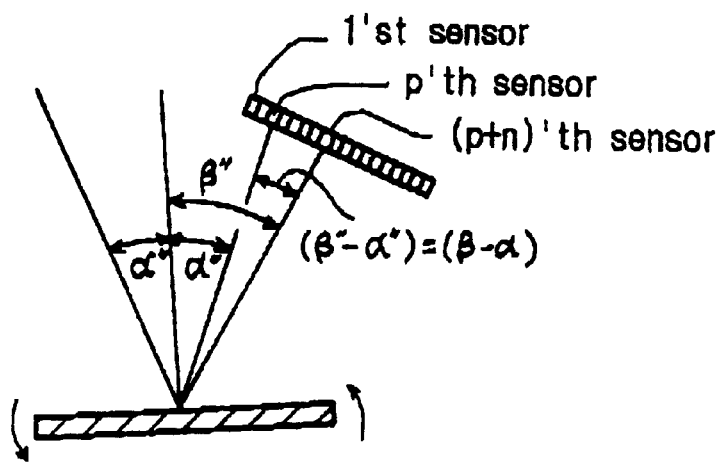

If the galvanized steel sheet is inclined to left or right due to external vibration, the angle of reflection of the specular reflection which is reflected by the galvanized steel sheet is changed form α to α' or α", whereas the angle of reflection of the scattering which is reflected by the galvanized steel sheet is also changed from β to β' or β" as shown in FIGS. 4(b) and 4(c).

Here, as the intensity of the specular reflection is always greater than those of other reflections reflected from the galvanized steel sheet, the photodiodes(m,p) by which the specular reflections are detected can be easily determined by comparing the intensities of reflections reflected from the steel sheet in computer (21). Also as described in the above, since the photodiode by which the intensity of the scattering is detected is determined relatively by the photodiode by which the intensity of the specular reflection is detected regardless of vibration of the galvanized steel sheet, the intensity of the scattering is detected by the photodiodes (m+n, P+n) which are apart from the photodiodes (m,p) by which the specular reflection is detected by a predetermined distance (n).

That is, as the intensity of the specular reflection is greater than the intensity of scattering regardless of whether the galvanized steel sheet, of which degree of alloying is to be measured, is affected by external vibration, it is possible to determine the photodiode by which the intensity of the specular reflection is detected by comparing the intensities of reflection detected by each photodiode in the computer (21). Accordingly, the intensity of scattering is determined to be the value which is detected by the photodiode which is apart from the photodiode by which the intensity of the specular reflection is detected by the computer (21) by a predetermined distance n. Therefore, the photodiode into which the specular reflection and scattering are injected may be determined easily, and it is possible to provide a reliable method of measuring the degree of alloying without any errors due to vibration by substituting the values detected by each photodiode into the above equations.

In the meantime, the photodiode arrays (16) detect, from the left, the intensity of the light for correcting change in output of the laser generator (11), the intensity of the specular reflection $I_2(α)$, and the intensity of scattering (β), produce the voltage which is proportional to the intensity of incident rays, and maintain the produced voltage. The photodiode array controller (20) discharges the voltages produced at a photodiodes of the photodiode arrays (16) in order of the one at the left first, recognizes the magnitude of discharge voltage which is amplified by the pre-amplifier (19), and inputs the magnitude of the voltage (i.e., intensity of incident ray) into the computer (21).

the computer (21) corrects the output of the laser generator (11) or computes the degree of alloying of the galvanized steel sheet (13) by analyzing signals of the photodiode arrays (16) according to the program built in. Here, the intensity of the light for correcting output of the laser generator (11) has a sharp Gaussian distribution, and therefore, is differentiated from the intensity of the specular reflection as well as the intensity of scattering. And as described in the above, since the intensity of the specular reflection is always greater than the intensity of the scattering, it is possible for the computer (11) to confirm the specular reflection readily.

Figure 3:
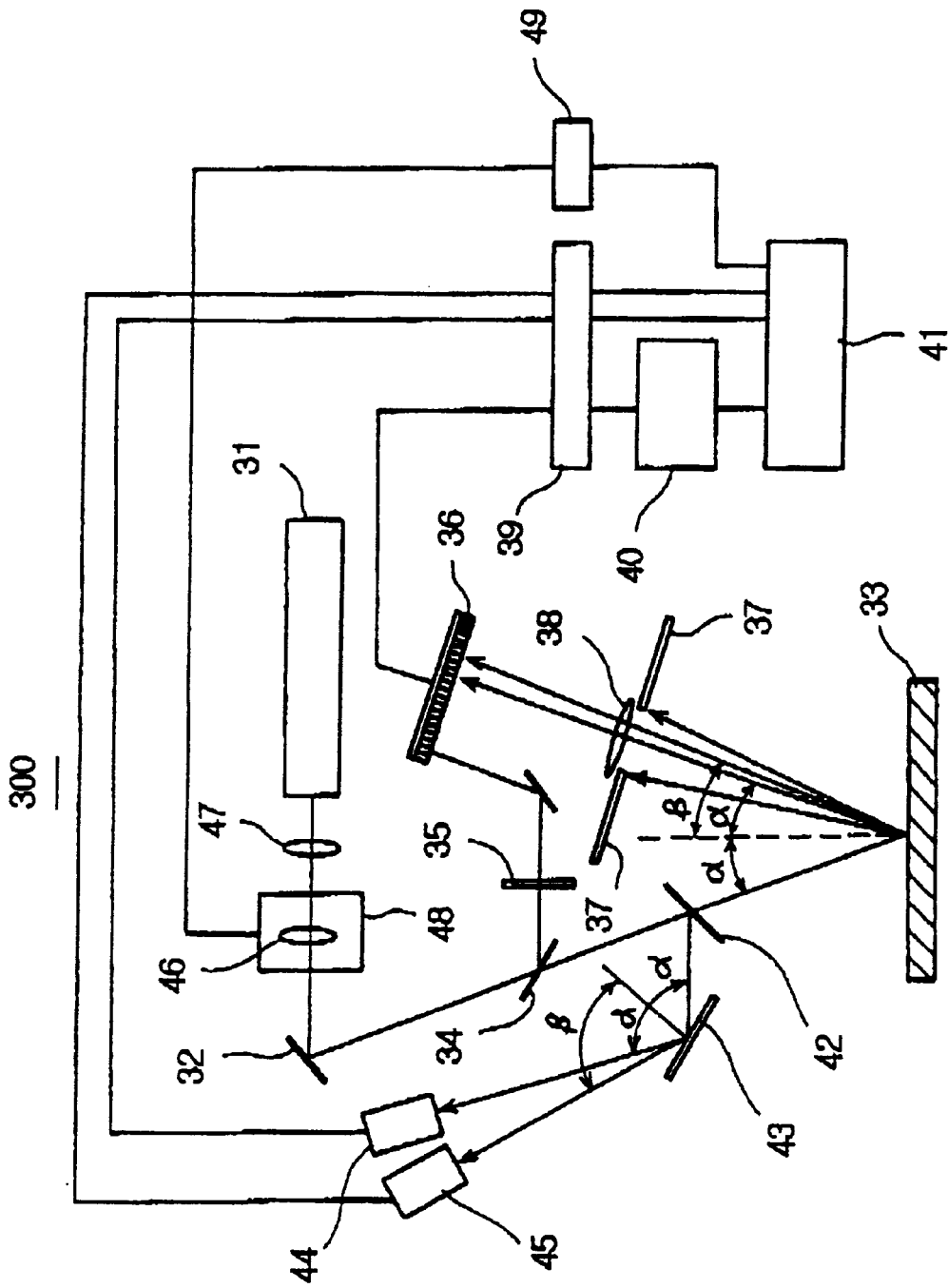
FIG. 3 is another outlined diagram of a measuring instrument for measuring the degree of alloying by using laser beams according to the present invention.

FIG. 3 is an outlined diagram of a measuring instrument (300) for measuring the degree of alloying to achieve another object of the present invention, which is similar to that in FIG. 2. However, the measuring instrument in FIG. 3 is different from that in FIG. 2 in that the one in FIG. 3 has two converging lenses (46)(47) having the same focal length (f) between the laser generator (31) and the mirror (32), and one of the converging lens (46) is mounted on the linear moving stage (48). The present invention having the above-described construction is useful for measuring the width of the galvanized steel sheet to be measured when measuring the degree of alloying of the galvanized steel sheet.

In general, it is necessary to measure the width of the galvanized steel sheet in order to measure the degree of alloying reliably whenever the coil-shaped galvanized steel sheet (33), of which degree of alloying is to be measured, is changed in the production line.

Therefore, in order to measure the width of the galvanized steel sheet (33), the lens (46) is moved first to have the distance of L<2f between the lens (46) and the lens (47) having the same focal length (f) by using the linear moving stage (48). And laser beams are generated from the laser generator (31), which are then projected through the lens (47), lens (46), mirror (32), first beam splitter (34), and second beams splitter (42), and are injected into the galvanized steel sheet 33 while moving the measuring instrument of the degree of alloying once from let to right and returning. The reflected lights are injected into the photodiode arrays (36), and the width Wo of the galvanized steel sheet (3) is measured by analyzing the values thus detected. The present inventors devised the present invention after learning that it was possible to confirm widthwise ends of the steel sheet by reducing the section area of laser beams scanned on the surface of the galvanized steel sheet.

In other words, as described in the above, measuring the width of the galvanized steel sheet can be carried out by freely controlling the cross-sectional area of laser beams which are injected onto the surface of the galvanized steel sheet by arranging the converging lens (46) mounted on a movable linear state (48) and another converging lens (47) having the same focal length between the laser generator (31) and the mirror (32) along the progression direction of the laser beams in a row. In more detail, in measuring the degree of alloying generally, the distance (L) between two lenses is set to be L=2f and the area of scanning is set to have a diameter of 5 mm as in the conventional measuring method. However, when measuring widthwise ends of the galvanized steel sheet, the area of scanning is reduced by collecting laser beams on the galvanized steel sheet by moving the lens (46) to have L<2f through the linear moving stage (48) and the linear moving stage controller (49) according to signals of the computer (41). As shown in FIG.

6, in measuring widthwise ends of the steel sheet, the reason for making the cross-sectional area of scanning small is because if the cross-sectional area of scanning of laser beams is reduced (for example, to 2 mm) by collecting laser beams through the lens, the intensity of reflection is greatly changed at the end of the steel sheet and it is possible to confirm that the current laser beam is at the end of the steel sheet through the photodiode arrays (36), whereas if the cross-sectional area of illumination of laser beams is made to have a diameter of 5 mm as in the conventional measurement of the degree of alloying, the change in the intensity of reflection at the end of the steel sheet is insignificant and it is not possible to confirm the ends.

After measuring the width Wo of the galvanized steel sheet (33), the lens (46) is moved by using the linear moving stage (48) so that the distance between the lens (46) and the lens (47) is L=2f. This is to perform usual measurement of the degree of alloying of the galvanized steel sheet continuously as shown below:

Firstly, the basic degree of alloying ($X_0$) of the standard sample is measured with the measuring instrument (300) arranged regularly. That is, laser beams are generated from the laser generator (31), are projected through the converging lenses (47)(48) having the same focal length (f) but separated by the distance of L=2f, and are injected onto the mirror (32). The laser beams reflected by the mirror (32) are divided into two rays at the first beam splitter (34). One ray is reflected and detected by one photodiode among photodiode arrays (36) which are composed of multiple photodiodes and arranged taking into consideration vibration of the galvanized steel sheet, while another ray penetrates through the first beam splitter (34) and is injected onto the standard sample (43) at an angle of incidence ($\alpha$) at the second beam splitter (42). Here, it is desirable to have an iris (35) in order to reduce the cross-sectional area of the incident ray between the first beam splitter (34) and the photodiode arrays (36). The ray detected by the photodiode arrays (36) is used for correcting the change in output of the laser generator (31). And the intensity of the specular reflection which is reflected by the standard sample (43) at an angle of reflection ($\alpha$) is detected by the photodetector (44), while the intensity of the scattering which is reflected at an angle of reflection ($\beta$) is detected by the photodetector (45). Then the basic degree of alloying ($X_0$) of the standard sample (43) is obtained by substituting the intensity of specular reflection $I_0(\alpha)$ and the intensity of scattering $I_0(\beta)$ detected by the photodetector (44) and another photodetector (45) into Equation (5). Specifically, the intensities of rays detected by the photodetector (44) and another photodetector (45) are amplified by the amplifier (39) and are inputted into the computer (41), and the basic degree of alloying is calculated according to the program built in.

Next, the comparative degree of alloying ($X_1$) of the standard sample is obtained by continuously obtaining the degree of alloying of the galvanized steel sheet (33) in the same method as obtaining the basic degree of alloying ($X_0$) of the above standard sample.

In other words, laser beams of the same intensity are used, which are injected onto lenses (46)(47), a mirror (32), first beam splitter (34), and second beam splitter (42). The second beam splitter (42) divides the laser beams into two rays. One ray is reflected and is injected onto the standard sample (43) at an angle of incidence ($\alpha$), while another ray penetrates and is injected onto the galvanized steel sheet (33). The intensity of specular reflection $I_1(\alpha)$ reflected by the standard sample (43) at an angle of reflection ($\alpha$) is detected by the photodetector (44), while the intensity of scattering $I_1(\beta)$ reflected at an angle of reflection ($\beta$) is detected by the photodetector (45). The comparative degree of alloying ($X_1$) of the standard sample is then obtained by substituting the above values thus detected into Equation (6). The comparative degree of alloying is also calculated within the above computer (41) as in calculating the basic degree of alloying.

Then an error between the comparative degree of alloying ($X_1$) of the standard sample and the basic degree of alloying ($X_0$) of the standard sample is obtained by comparing these two values. Whether the arrangement of the laser generator (31), mirror (32), first beam splitter (34), and second beam splitter (42) is superior may be confirmed according to whether the above error is within a predetermined range.

If the arrangement is confirmed to be superior, the degree of alloying of the galvanized steel sheet (33) is obtained. On the other hand, if the arrangement is confirmed to be inferior, the arrangement of the laser generator (31), mirror (32), first beam splitter (34), and second beam splitter (42) is corrected, after which the degree of alloying of the galvanized steel sheet (33) is obtained. Such construction of the present invention can give reliability to the results of measuring the degree of alloying of the galvanized steel sheet (33).

The degree of alloying of the galvanized steel sheet (33) may be obtained simultaneously with the comparative degree of alloying ($X_1$) of the standard sample.

In obtaining the degree of alloying ($X_1$) of the standard sample, the laser beams generated from the laser generator (31) go through the mirror (32) and the first beam splitter (34), are injected onto the second beam splitter (42), are divided into two rays, and are reflected and projected. Between these, the projected ray is injected onto the galvanized steel sheet (33). The ray injected onto the galvanized steel sheet (33) at an angle of incidence ($\alpha$) is reflected by the galvanized steel sheet. The intensity of specular reflection $I_2(\alpha)$ reflected at an angle of reflection ($\alpha$) is detected by one photodiode among photodiode arrays (36) which are composed of multiple photodiodes and are arranged taking into consideration the vibration of the galvanized steel sheet, while the intensity of scattering $I_2(\beta)$ reflected at an angle of reflection ($\beta$) is detected by another photodiode among photodiode arrays (36) which are apart from the photodiode, into which the specular reflection is injected, by a predetermined distance n.

The degree of alloying ($X_2$) of the galvanized steel sheet (33) is then obtained by substituting the intensity of specular reflection $I_2(\alpha)$ and the intensity of scattering $I_2(\beta)$ which are detected by the photodiode arrays (36) into Equation (7). Here, since the intensity of the specular reflection $I_2(\alpha)$ is always greater than the intensity of the scattering $I_2(\beta)$, the computer (41) is able to confirm readily the photodiode by which the intensity of the specular reflection is detected, and the photodiode by which the intensity of the scattering is detected may be also determined by the predetermined distance n which is stored in the computer (41).

It is desirable to have a lens (38) and masks (37) at both ends of the lens (38) between the galvanized steel sheet (33) and photodiode arrays (36). The lens (38) converts the reflection into parallel rays, while the masks (37) pass through the specular reflection or scattering and prevent mixing of the light which is reflected by the surface of the galvanized steel sheet and the light which is reflected by the first beam splitter (34).

And the photodiode arrays (36) are composed of arrayed multiple photodiodes. It is desirable that they are arranged in the normal direction with respect to the specular reflection which is reflected by the vibration-free galvanized steel sheet (33) at an angle of reflection ($\alpha$). Such construction of photodiode arrays (36) is effective in eliminating errors due to vibration when measuring the degree of alloying. The reason for it is described in the above and is not illustrated here.

The degree of alloying ($X_2$) of the galvanized steel sheet (33) is then measured continuously by repeating the above steps while moving the measuring instrument (300) in the widthwise direction of the galvanized steel sheet within the width ($W_0$) obtained in the above.

Figure 5A:
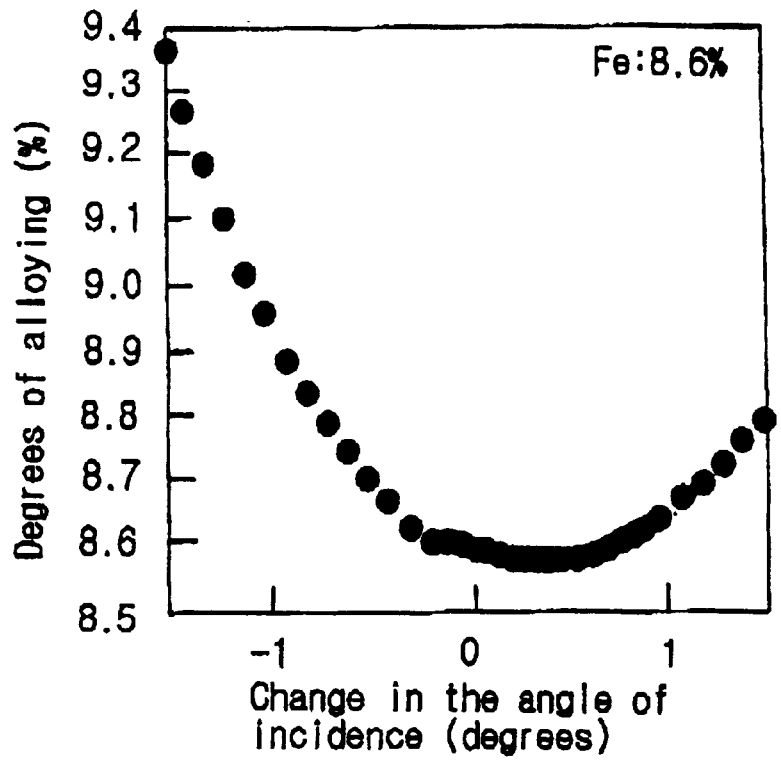
FIGS. 5(*a*) and 5(*b*) are graphs showing errors in the measurement due to disarray of photodiode elements.
Figure 5B:
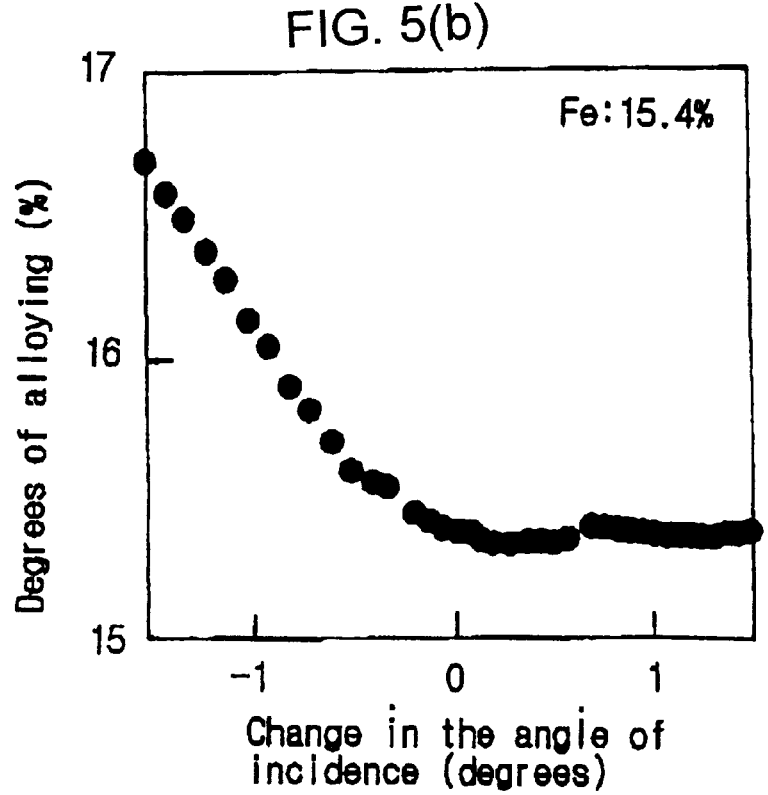
Figure 6:
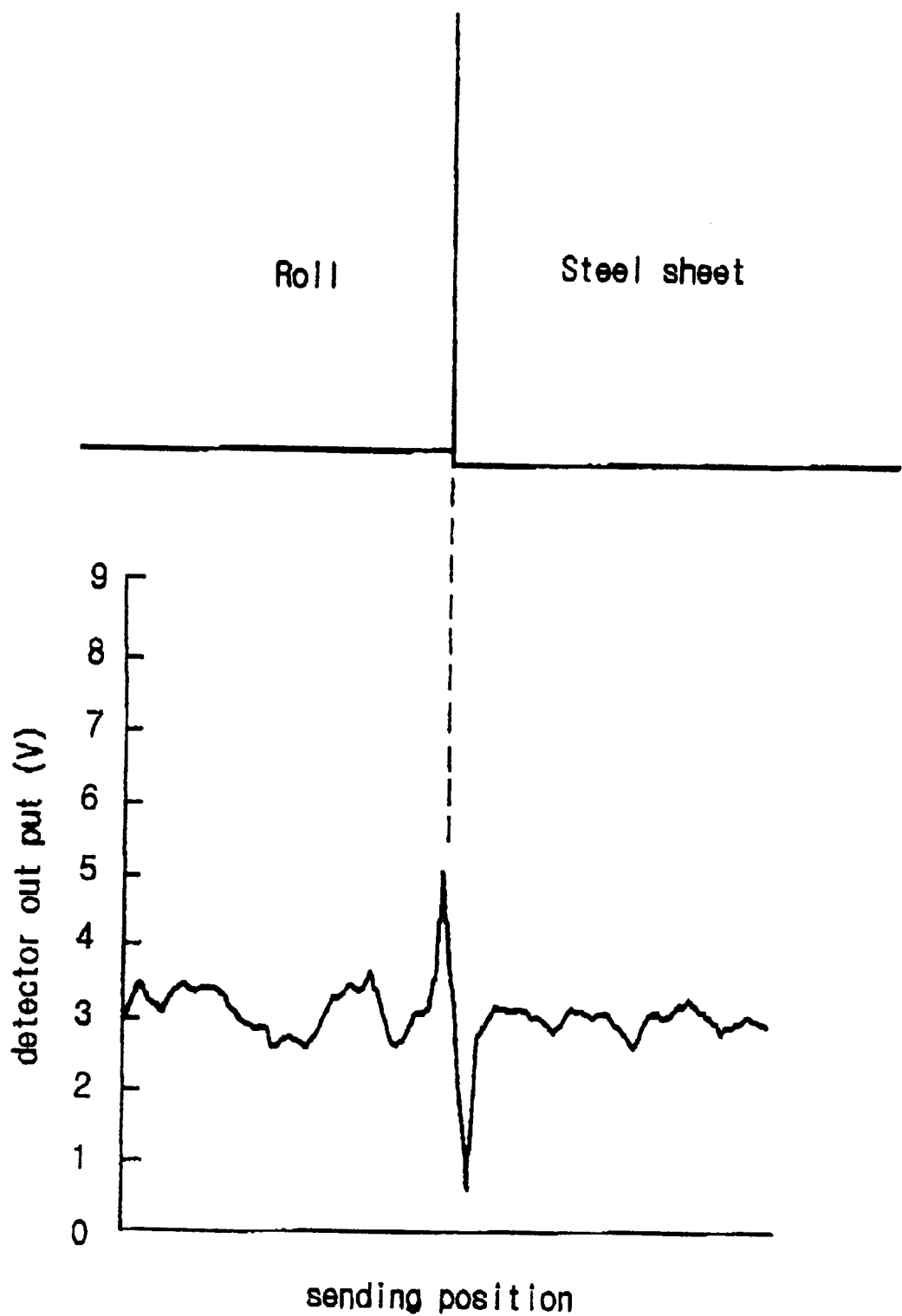
FIG. 6 shows the signal diagram of ends of the steel sheet of the present invention.

FIGS. 5(a) and 5(b) are graphs showing errors in the measurement according to the change in the angle of incidence of laser beams as the position of the mirror (12) among photodiode elements is deviated from its original fixed position. FIGS. 5(a) and 5(b) show the changes in the degree of alloying which occur as the angle of incidence of laser beams is varied from the original angle of measurement, where the degrees of alloying of the samples used for the measurement are 8.6% Fe and 15.37% Fe, respectively.

Figure 7:
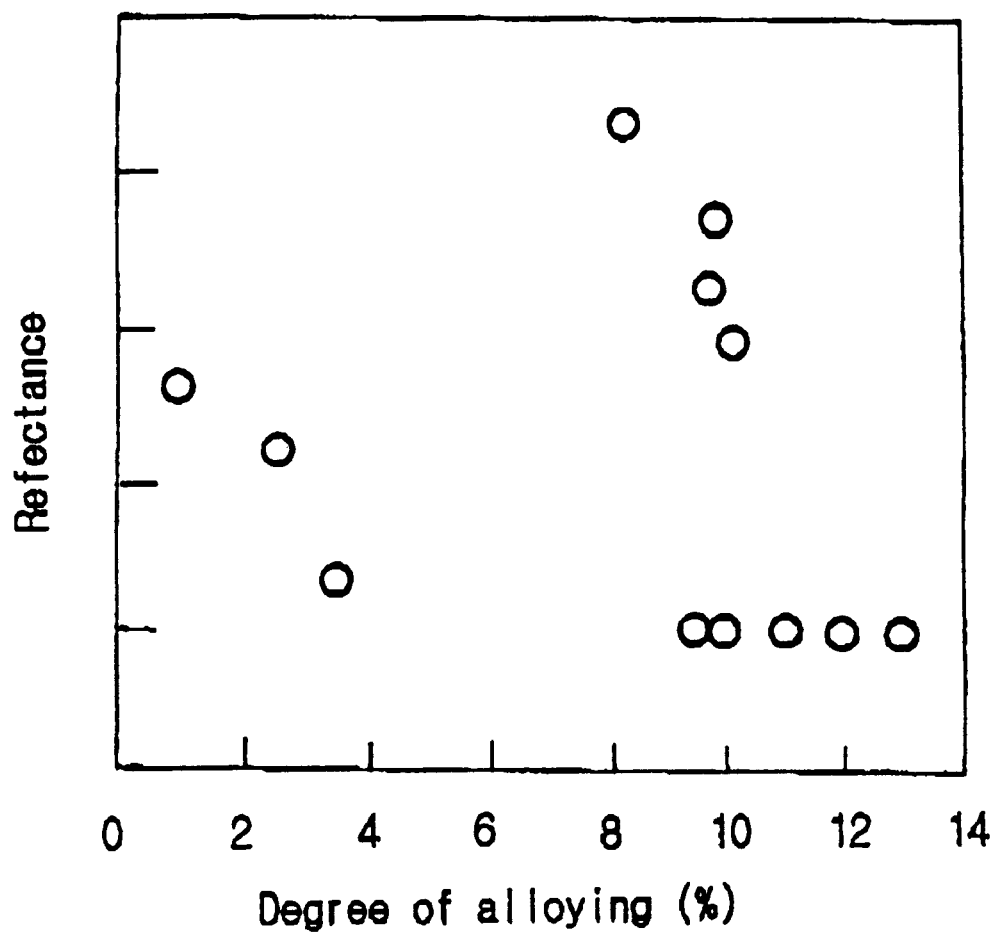
FIG. 7 is a graph showing the results of measurement of the degree of alloying according to a prior art measurement method.

FIG. 7 shows a comparative example measuring the relationship between the reflectance and the degree of alloying according to the conventional method. The reflectance and degree of alloying do not show a consistent relationship due to the effects of surface roughness of the galvanized steel sheet, surrounding lights, etc.

FIG. 8 shows the results of measuring the degree of alloying according to the method of measurement of the present invention, from which it is seen that the reflectance and degree of alloying are measured accurately.

Accordingly, the construction of the present invention as described in the above is effective in providing a method of measuring the degree of alloying in which errors in the measurement due to the vibration are eliminated and the width of the galvanized steel sheet is measured in real time when measuring the degree of alloying of the galvanized steel sheet.

While the invention has been described in terms of a few preferred embodiments, those skilled in the art will recognize that the invention can be practiced with modification within the spirit and scope of the appended claims.

What is claimed is:

1. A method of measuring the degree of alloying using laser beams comprising the steps of:

directing a laser beam onto a mirror (12) which is located at a standard position from a laser generator (11), dividing said laser beam reflected from said mirror (12) into two rays at a first beam splitter (14) which is located at a standard position, directing one ray into one photodiode among photodiode arrays (16) which are composed of multiple photodiodes and arranged taking into consideration vibration of a galvanized steel sheet, and projecting another ray through said first beam splitter (14) and directing said ray onto a standard sample (23) at an angle of incidence ($\alpha$) at a second beam splitter (22) which is located at a standard position;

detecting intensity of specular reflection $I_O(\alpha)$ which is reflected at an angle of reflection ($\alpha$) by said standard sample (23) with a first photodetector (24), and detecting intensity of scattering $I_0(\beta)$ which is reflected at an angle of reflection ($\beta$) with a second photodetector (25);

obtaining the basic degree of alloying ($X_0$) of said standard sample (23) by substituting intensity of specular reflection $I_0(\alpha)$ and intensity of scattering $I_0(\beta)$ thus detected into the following equation:

$$X_0(\%) = k \frac{\ln \frac{I_0(\alpha)}{I_0(\beta)}}{I_0(\alpha)}$$

where k is a proportional constant:

generating laser beams from said laser generator (11) under the same conditions for those of obtaining the basic degree of alloying ($X_0$), and directing one of beams, which are divided at said second beam splitter (22) after being reflected by said mirror (12) and after passing through said first beam splitter (14), onto said standard sample (23) at an angle of incidence ($\alpha$);

detecting intensity of specular reflection $I_1(\alpha)$ reflected by said standard sample (23) at an angle of reflection ($\alpha$) with said photodetector (24), and detecting intensity of scattering $I_1(\beta)$ reflected at an angle of reflection ($\beta$) with said photodetector (25);

obtaining the comparative degree of alloying ($X_1$) of said standard sample (23) by substituting intensity of specular reflection $I_1$ ($\alpha$) and intensity of scattering $I_1$ ($\beta$) thus detected into the following equation:

$$X_1(\%) = k \frac{\ln \frac{I_1(\alpha)}{I_1(\beta)}}{I_1(\alpha)}$$

where k is a proportional constant;

obtaining an error between the basic degree of alloying ($X_0$) of said standard sample (23) and the comparative degree of alloying ($X_1$) of said standard sample (23) by comparing these two values thus obtained, and correcting arrangement of said laser generator (11), said mirror (12), said first beam splitter (14), and said second beam splitter (22) so that said error is within a predetermined range;

generating laser beams from said laser generator (11) under the same conditions for those of obtaining the basic degree of alloying ($X_0$), and directing said beam, which is injected onto said second beam splitter (22) and is projected after being reflected by said mirror (12) and passing through said first beam splitter (14), onto said galvanized steel sheet (13) at an angle of incidence ($\alpha$), after correcting arrangement of said laser generator (11), said mirror (12), said first beam splitter (14), and said second beam splitter (22);

detecting intensity of specular reflection $I_2(\alpha)$ reflected by said galvanized steel sheet (13) with a first photodiode among photodiode arrays (16) which are composed of multiple photodiodes and are arranged taking into consideration vibration of said galvanized steel sheet, and detecting intensity of scattering reflect $I_2(\beta)$ with a second photodiode among photodiode arrays (16) which are apart at a predetermined distance n from said first photodiode by which the specular reflection is detected; and obtaining the degree of alloying ($X_2$) of a galvanized steel sheet by substituting intensity of specular reflection $I_2(\alpha)$ and intensity of scattering $I_2(\beta)$ thus detected into the following equation:

$$X_2(\%) = k\frac{\ln\frac{I_2(\alpha)}{I_2(\beta)}}{I_2(\alpha)}$$

where k is a proportional constant.

2. The method of measuring the degree of alloying using laser beams of claim 1 wherein there are a converging lens (18) and two masks (17) at both ends of said converging lens (18) between said galvanized steel sheet (13) and said photodiode arrays (16).

3. The method of measuring the degree of alloying using laser beams of claim 1 wherein said photodiode arrays (16) are arranged in the normal direction with respect to specular reflection which is reflected at an angle of reflection ($\alpha$) by said galvanized steel sheet which is not subject to vibration.

4. A method of measuring the degree of alloying using laser beams comprising the steps of:

measuring a width $W_0$ of a galvanized steel sheet (33) by generating laser beams from a laser generator (31) while moving a first converging lens mounted on a linear moving stage (48) such that a distance "L" between said first converging lens (46) and a second converging lens (47) having the same focal length (f) is L<2f, directing a beam, which is projected through said converging lens (47), said converging lens (48), and reflected by a mirror (32), through a first beam splitter (34) and second beam splitter (42), onto said galvanized steel sheet (33) while running a measuring instrument left and right once, and analyzing an intensity of reflection detected by photodiode arrays (36);

moving said converging lens (46) mounted on said linear moving stage (48) such that said distance "L" between said converging lens (46) and said converging lens (47) is L=2f after measuring the width $W_0$ of said galvanized steel sheet;

directing the laser beam through said converging lens (46) and said converging lens (47), which are located at a standard position from a laser generator (31) and are apart from each other by the distance "L" of 2f, and directing the laser beam onto said mirror (32) which is located at the standard position, dividing said laser beam reflected from said mirror (32) into two rays at said first beam splitter (34) which is located at a standard position, a first ray being detected with a first photodiode among the photodiode arrays (36) which are composed of multiple photodiodes and are arranged taking into consideration vibration of said galvanized steel sheet (33), while a second ray penetrating through said first beam splitter (34) and directing said second ray onto a standard sample (43) at said second beam splitter (42), which is located at said standard position, at an angle of incidence ($\alpha$);

detecting an intensity of specular reflection $I_0(\alpha)$ reflected by said standard sample (43) at an angle of reflection ($\alpha$) with a first photodetector (44), and detecting an intensity of scattering $I_0(\beta)$ reflected at an angle of reflection ($\beta$) with a second photodetector (45);

obtaining the basic degree of alloying ($X_0$) of said standard sample (43) by substituting the intensity of specular reflection $I_0(\alpha)$ and the intensity of scattering $I_0(\beta)$ thus detected into the following equation:

$$X_0(\%) = k\frac{\ln\frac{I_0(\alpha)}{I_0(\beta)}}{I_0(\alpha)}$$

where k is a proportional constant;

generating a laser beam from said laser generator (31) under the same conditions for those of obtaining the basic degree of alloying ($X_0$), and directing the beam, which is divided at said second beam splitter (42) after being reflected by said mirror (32) and passing through said first beam splitter (34), on said standard sample (43) at an angle of incident ($\alpha$);

detecting the intensity of specular reflection $I_1(\alpha)$ reflected by said standard sample (43) at an angle of reflection ($\alpha$) with the first photodetector (44), and detecting the intensity of scattering $I_2(\beta)$ reflected at an angle of reflection ($\beta$) with the second photodetector (45);

obtaining the comparative degree of alloying ($X_1$) of said standard sample (43) by substituting the intensity of specular reflection $I_1(\alpha)$ and the intensity of scattering $I_1(\beta)$ thus detected into the following equation:

$$X_1(\%) = k\frac{\ln\frac{I_1(\alpha)}{I_1(\beta)}}{I_1(\alpha)}$$

where k is a proportional constant;

obtaining an error between the basic degree of alloying ($X_0$) of said standard sample (43) and the comparative degree of alloying ($X_1$) of said standard sample (43) by comparing these two values thus obtained, and correcting the arrangement of said laser generator (31), said mirror (32), said first beam splitter (34), and said second beam splitter (42) so that said error is within a predetermined range;

generating a laser beam from said laser generator (31) under the same conditions for those of obtaining the basic degree of alloying ($X_0$), and directing said beam onto said second beam splitter (42) after being reflected by said mirror (32) and passing through said first beam splitter (34), and projecting the beam onto said galvanized steel sheet (33) at an angle of incidence ($\alpha$), after correcting arrangement of said laser generator (31), said mirror (32), said first beam splitter (34), and said second beam splitter (42);

detecting the intensity of specular reflection $I_2(\alpha)$ reflected by said galvanized steel sheet (33) with a first photodiode among photodiode arrays (36) which are composed of multiple photodiodes and are arranged taking into consideration vibration of said galvanized steel sheet (33), and detecting intensity of scattering reflected $I_2(\beta)$ with a second photodiode among photodiode arrays (36) which are apart at a predetermined distance n from said photodiode by which the specular reflection is detected;

obtaining the degree of alloying ($X_2$) of said galvanized steel sheet (33) by substituting the intensity of specular reflection $I_2(\alpha)$ and the intensity of scattering $I_2(\beta)$ thus detected into the following equation:

$$X_2(\%) = k \frac{\ln \frac{I_2(\alpha)}{I_2(\beta)}}{I_2(\alpha)}$$

where k is a proportional constant; and obtaining the degree of alloying ($X_2$) of said galvanized steel sheet (33) continuously by repeating said steps while moving said measuring instrument in the widthwise direction within the width ($W_2$).

5. The method of measuring the degree of alloying laser beams of claim 4 wherein there are a converging lens (38) and two masks (37) at both ends of said converging lens (38) between said galvanized steel sheet (33) and said photodiode arrays (36).

6. The method of measuring the degree of alloying using laser beams of claim 4 wherein said photodiode arrays (36) are arranged in the normal direction with respect to specular reflection which is reflected at an angle of reflection ($\alpha$) by said galvanized steel sheet (33) which is not subject to vibration.

7. The method of measuring the degree of alloying using laser beams of claim 2, wherein said photodiode arrays are arranged in the normal direction with respect to specular reflection which is reflected at an angle of reflection by said galvanized steel sheet which is not subject to vibration.

8. The method of measuring the degree of alloying using laser beams of claim 5, wherein said photodiode arrays are arranged in the normal direction with respect to specular reflection which is reflected at an angle of reflection by said galvanized steel sheet which is not subject to vibration.

* * * * *

UNITED STATES PATENT AND TRADEMARK OFFICE
CERTIFICATE OF CORRECTION

PATENT NO. : 6,137,583
DATED : October 24, 2000
INVENTOR(S) : Dal Woo Kim, et. al.

It is certified that error appears in the above-identified patent and that said Letters Patent is hereby corrected as shown below:

Title Page [73] ASSIGNEE insert additional assignee --Research Institute of Industrial Science & Technology, Rep. of Korea--.

Column 2, Line 3, "layer,," should read --layer,--.

Column 2, Lines 39-42

$$X_0(\%) = k \ln \frac{\frac{I_0(a)}{I_0(\beta)}}{I_0(a)}$$

should read $$X_0(\%) = k \frac{\ln \frac{I_0(a)}{I_0(\beta)}}{I_0(a)}$$

Column 3, Lines 60-63

$$X_0(\%) = k \ln \frac{\frac{I_0(a)}{I_0(\beta)}}{I_0(a)}$$

should read $$X_0(\%) = k \frac{\ln \frac{I_0(a)}{I_0(\beta)}}{I_0(a)}$$

UNITED STATES PATENT AND TRADEMARK OFFICE
CERTIFICATE OF CORRECTION

Page 2 of 5

PATENT NO. : 6,137,583
DATED : October 24, 2000
INVENTOR(S) : Dal Woo Kim, et. al.

It is certified that error appears in the above-identified patent and that said Letters Patent is hereby corrected as shown below:

Column 4, Lines 16-18

$$X_1(\%) = k \ln \frac{\frac{I_1(a)}{I_1(\beta)}}{I_1(a)}$$

should read $$X_1(\%) = k \frac{\ln \frac{I_1(a)}{I_1(\beta)}}{I_1(a)}$$

Column 4, Line 42, "of the vibration" should read --the vibration of--.

Column 4, Lines 52-55

$$X_2(\%) = k \ln \frac{\frac{I_2(a)}{I_2(\beta)}}{I_2(a)}$$

should read $$X_2(\%) = k \frac{\ln \frac{I_2(a)}{I_2(\beta)}}{I_2(a)}$$

UNITED STATES PATENT AND TRADEMARK OFFICE
CERTIFICATE OF CORRECTION

PATENT NO. : 6,137,583
DATED : October 24, 2000
INVENTOR(S) : Dal Woo Kim, et. al.

It is certified that error appears in the above-identified patent and that said Letters Patent is hereby corrected as shown below:

Column 5, Lines 33-35

$$X_1(\%) = k \ln \frac{\frac{I_1(\alpha)}{I_1(\beta)}}{I_1(\alpha)}$$

should read $$X_0(\%) = k \frac{\ln \frac{I_0(\alpha)}{I_0(\beta)}}{I_0(\alpha)}$$

Column 5, Lines 56-58

$$X_2(\%) = k \ln \frac{\frac{I_2(\alpha)}{I_2(\beta)}}{I_2(\alpha)}$$

should read $$X_2(\%) = k \frac{\ln \frac{I_2(\alpha)}{I_2(\beta)}}{I_2(\alpha)}$$

UNITED STATES PATENT AND TRADEMARK OFFICE
CERTIFICATE OF CORRECTION

PATENT NO. : 6,137,583
DATED : October 24, 2000
INVENTOR(S) : Dal Woo Kim, et. al.

It is certified that error appears in the above-identified patent and that said Letters Patent is hereby corrected as shown below:

Column 6, Lines 24-26

$$X_1(\%) = k \frac{\ln \frac{I_1(a)}{I_1(\beta)}}{I_1(a)}$$

should read $$X_2(\%) = k \frac{\ln \frac{I_2(a)}{I_2(\beta)}}{I_2(a)}$$

Column 9, Line 22, "form" should read --from--.

Column 9, Line 65, after "at" insert --a--.

Column 10, Line 2, "the" should read --The--.

Column 10, Line 13, "computer (11)" should read --computer (21)--.

Column 10, Line 40, "beams" should read --beam--.

Column 10, Line 42, "let" should read --left--.

Column 10, Line 55, "state" should read --stage--.

UNITED STATES PATENT AND TRADEMARK OFFICE
CERTIFICATE OF CORRECTION

PATENT NO. : 6,137,583
DATED : October 24, 2000
INVENTOR(S) : Dal Woo Kim, et. al.

It is certified that error appears in the above-identified patent and that said Letters Patent is hereby corrected as shown below:

Claim 1, Line 60, Column 13, "$I_o(\alpha)$" should read --$I_0(\alpha)$--.

Claim 4, Line 29, Column 15, delete "(48)" and insert --(46)--.

Claim 4, Line 19, Column 16, "$I_2(\beta)$" should read --$I_1(\beta)$--.

Signed and Sealed this

Twenty-second Day of May, 2001

*Attest:*

NICHOLAS P. GODICI

*Attesting Officer*     *Acting Director of the United States Patent and Trademark Office*